United States Patent [19]
Dorros

[11] Patent Number: 5,720,735
[45] Date of Patent: Feb. 24, 1998

[54] BIFURCATED ENDOVASCULAR CATHETER

[76] Inventor: Gerald Dorros, 8130 N. Beach Dr., Milwaukee, Wis. 53217

[21] Appl. No.: 799,743

[22] Filed: Feb. 12, 1997

[51] Int. Cl.$^6$ ................................................ A61M 25/00
[52] U.S. Cl. ...................................... 604/284; 606/194
[58] Field of Search ............................ 604/284, 283, 604/281, 280, 264; 606/191–195

[56] References Cited

U.S. PATENT DOCUMENTS

| | | | |
|---|---|---|---|
| 3,435,824 | 4/1969 | Gamponia | 128/334 |
| 4,248,224 | 2/1981 | Jones | 128/214 R |
| 4,309,994 | 1/1982 | Grunwald | 128/214 R |
| 4,413,989 | 11/1983 | Schjeldahl | 604/96 |
| 4,456,000 | 6/1984 | Schjeldahl et al. | 128/1 D |
| 4,734,094 | 3/1988 | Jacob et al. | 604/284 |
| 4,896,670 | 1/1990 | Crittenden | 606/194 |
| 5,041,126 | 8/1991 | Gianturco | 606/195 |
| 5,143,095 | 9/1992 | Sahota | 128/898 |
| 5,413,581 | 5/1995 | Goy | 606/194 |

*Primary Examiner*—John D. Yasko
*Attorney, Agent, or Firm*—Quarles & Brady

[57] ABSTRACT

An endovascular catheter for use in PTA, PTCA and other endovascular procedures has a bifurcated distal end with two branches. Each catheter branch may be guided into a separate vessel branch, and endovascular devices such as balloons, stents, stent grafts, or grafts may be precisely deployed in bifurcated vessels. Separate endovascular devices may be deployed in either vessel branch or the vessel trunk or an integral device may be simultaneously deployed in both branches and the trunk.

12 Claims, 6 Drawing Sheets

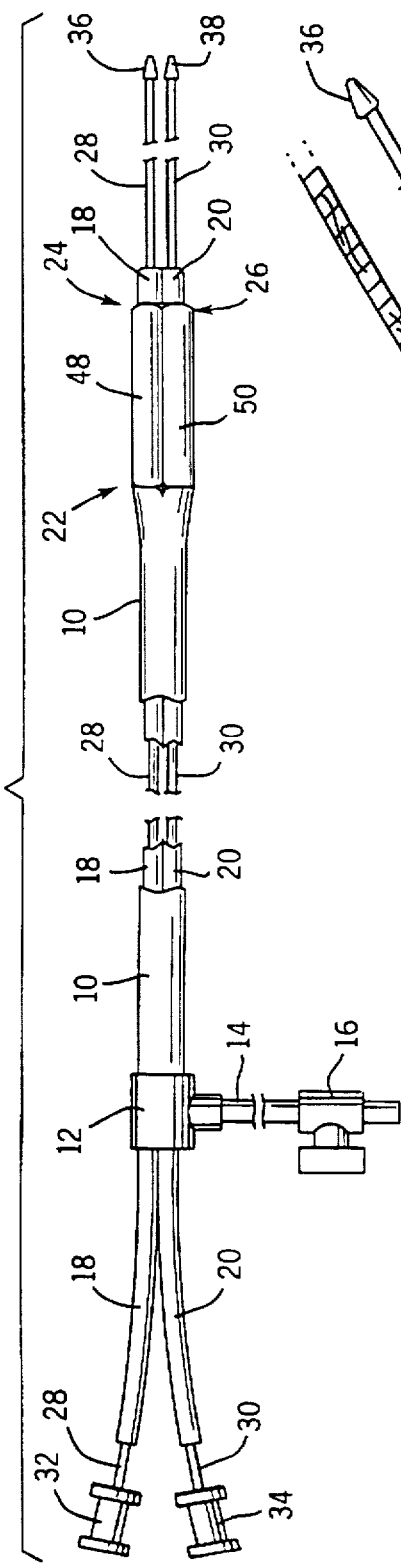
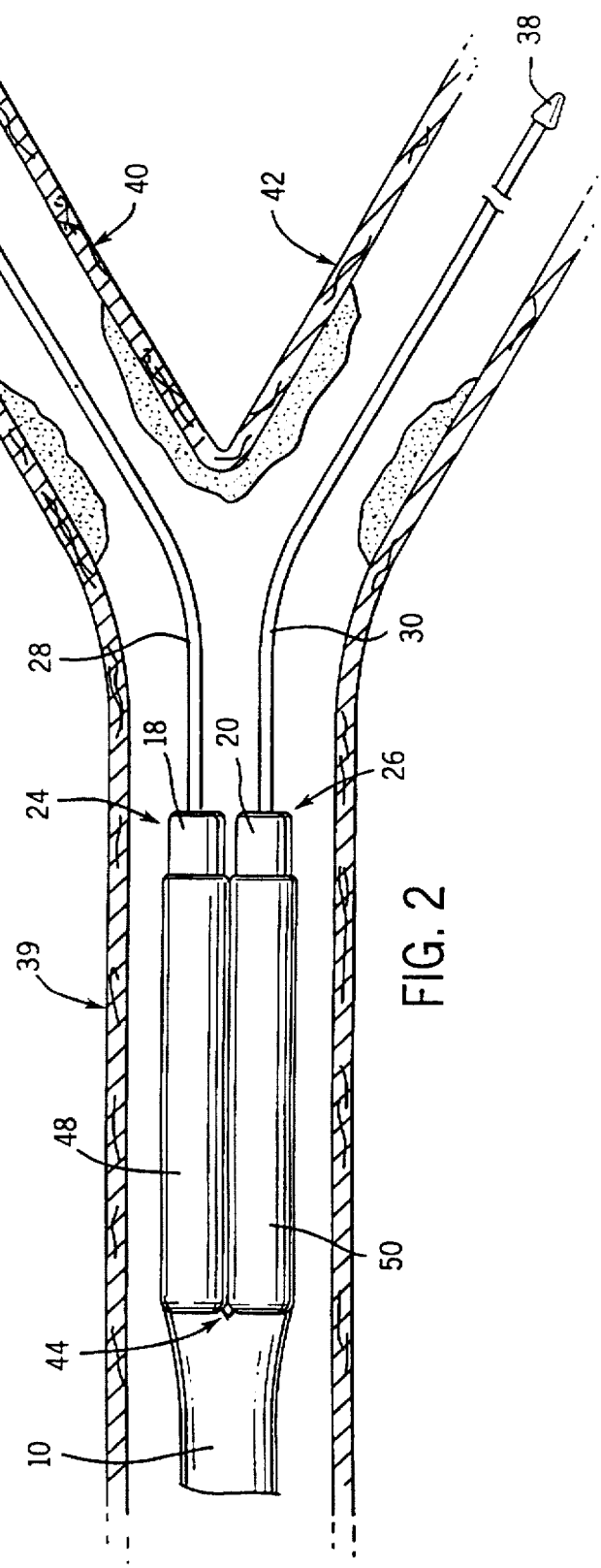
FIG. 1
FIG. 2

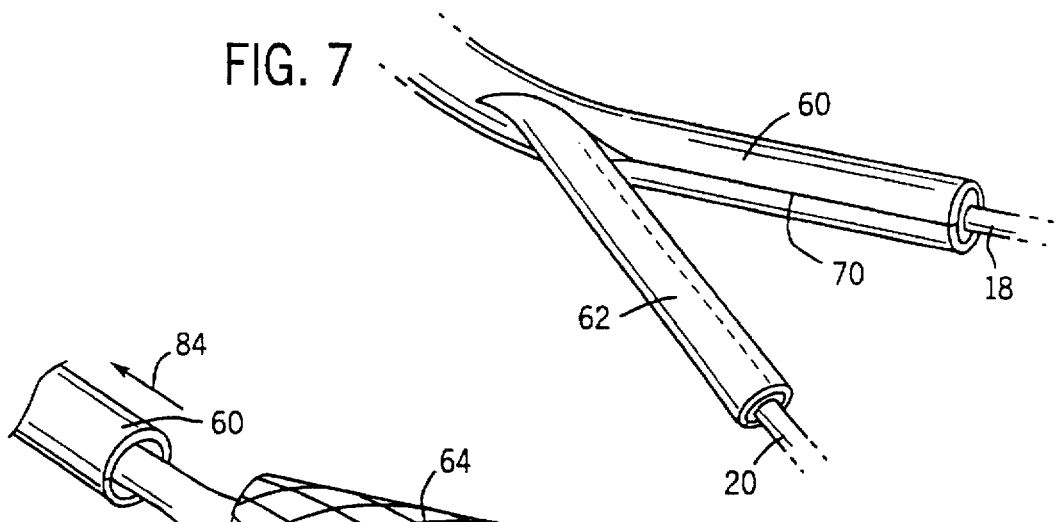
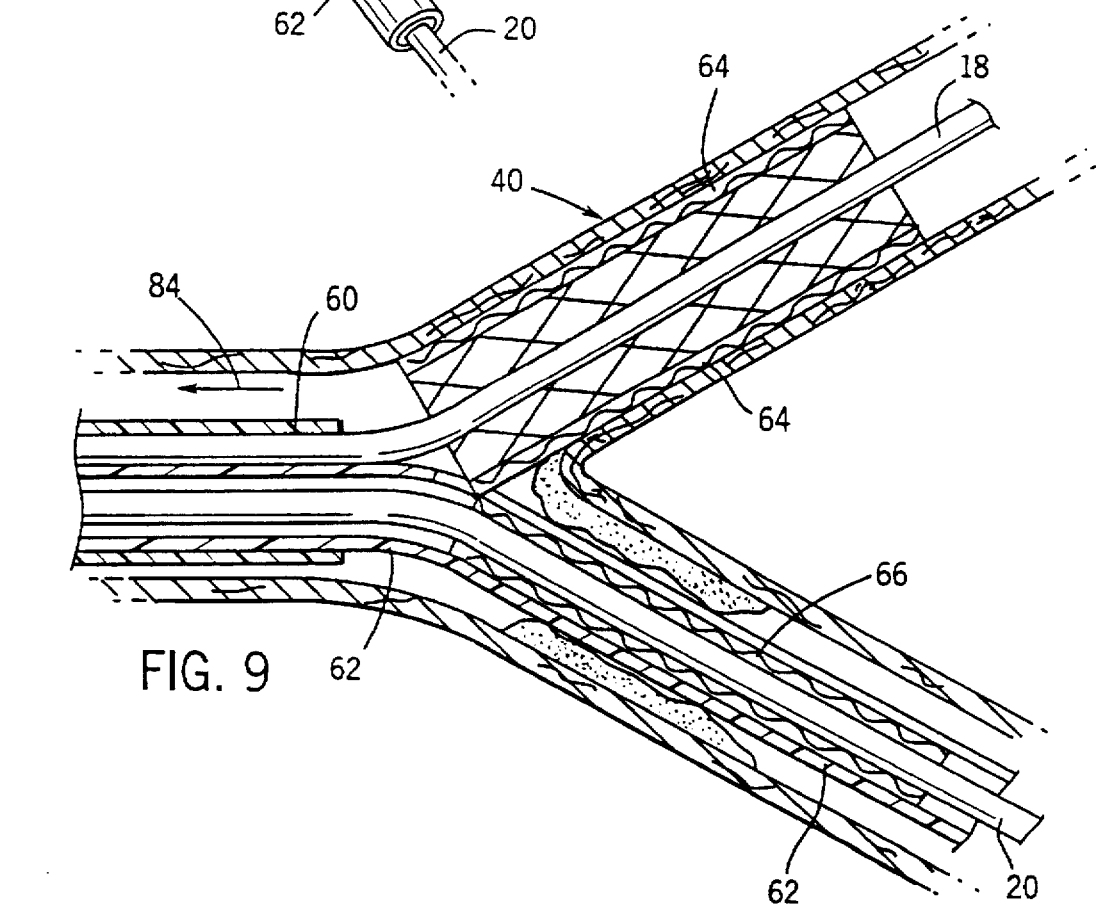

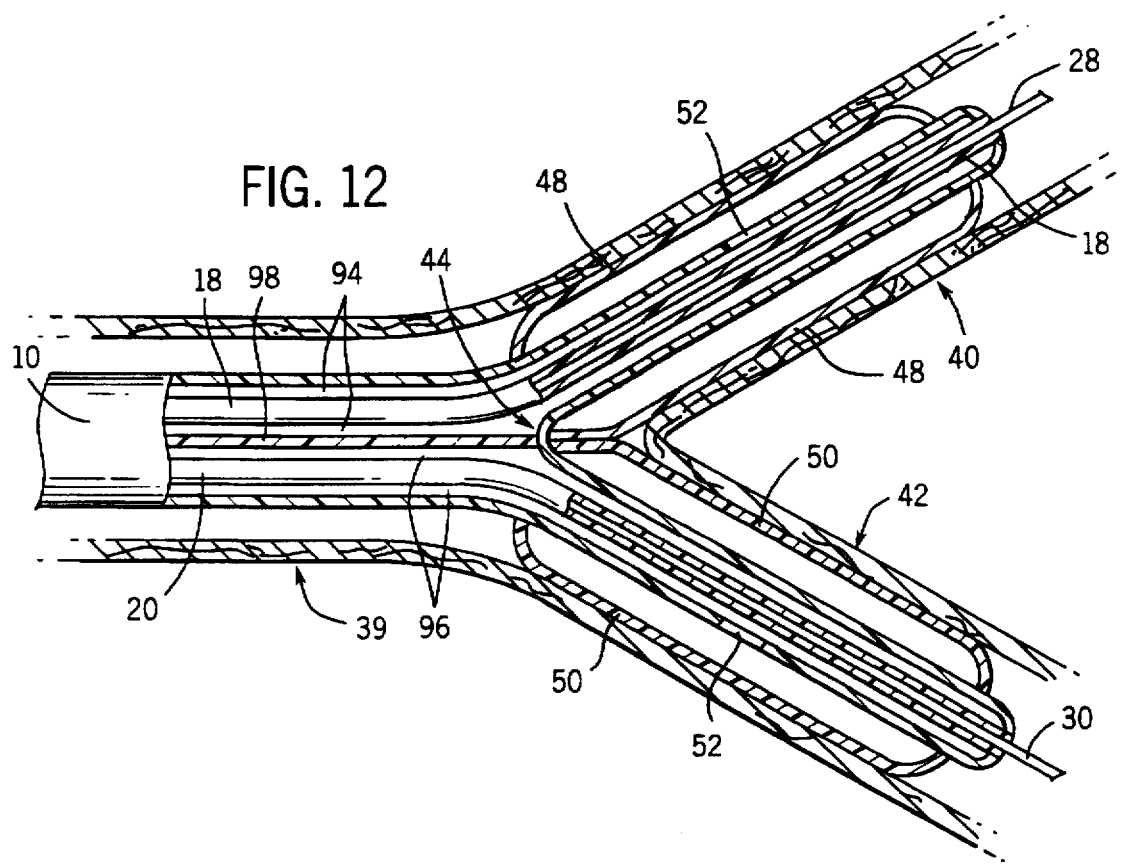

BIFURCATED ENDOVASCULAR CATHETER

BACKGROUND OF THE INVENTION

The field of the invention is endovascular catheters used to deliver devices such as balloons to recanalize vessels or to place and deploy endovascular grafts or stents within the vessel.

Percutaneous transluminal coronary angioplasty (PTCA) and percutaneous transluminal angioplasty (PTA), procedures for treating a patient having a stenosis (constricted), or occluded blood vessel region in a coronary or peripheral artery, have become widely accepted therapeutic alternatives to coronary and peripheral arterial bypass surgery for many patients. PTCA and PTA increase the vessel lumen by radial expansion of the plaque or other pathology which causes the stenosis or occlusion through "controlled" tearing of the vessel lining. The principal advantage of the PTCA or PTA procedure over other surgical procedures is its ability to enlarge the narrowed vessel or recanalize the occluded vessel at a lower or reduced morbidity and mortality. It often eliminates the immediate post-operative discomforts associated with coronary or peripheral bypass surgery, reducing hospital costs, and more rapidly returning the patient to work or allowing performance of activities of daily life.

Many different catheter structures have been designed to deliver balloons and/or devices through the vessel lumen to the diseased vessel segment. An entry needle is used to gain access to a vessel percutaneously or directly if the vessel is exposed by a small incision. A guide wire is introduced. A sheath is placed into the arterial (or venus) access site. The guide wire is fed through the vasculature to the diseased vessel and then across the diseased vessel segment. A hollow catheter is then introduced and fed over the guide wire until its distal end reaches the diseased vessel segment. The catheter may carry a balloon or distensible distal segment on its end, which is then inflated through a separate lumen inside the catheter to expand outward against the vessel wall and dilate it. This method is used, for example, to treat coronary stenoses and other vascular obstructions.

Another commonly used procedure uses a catheter to deliver a stent to the diseased vessel segment. In this procedure, the stent is transported on the end of the catheter to the diseased vessel and the stent is deployed by self-expansion, balloon expansion, thermal memory or some other mechanism. The stent expands outward against the interior of the vessel wall to dilate the vessel and serve as a vessel infrastructure which will maintain the dilated lumen size after the catheter is withdrawn.

A variety of devices have been used as intraluminal stents: "coiled" stainless steel springs, helical wound coil springs, expandable stainless steel woven or zig-zag pattern structures, stainless steel expandable structures, biodegradable or synthetic non-reabsorbable structure, or structures formed with materials having a thermal "memory". They all deploy in a circular cylindrical shape and are sized for the particular diseased vessel.

A graft, is a conduit constructed of synthetic material or from veins or arteries. It is usually impermeable or semipermeable and becomes impermeable when implanted in the body. Therefore, a graft can replace a section of diseased (stenotic, occluded or aneurysmal) vasculature.

The precise positioning of the balloon, stent or graft within the diseased vessel is critical to the success of the procedure. Considerable time may be required by the surgeon or interventionist to guide the catheter into the proper vessel and precisely align the endovascular device carried on its end with the diseased vessel segments. The human vascular tree is far from uniform in structure and each procedure is a unique experience requiring considerable manual dexterity. With currently available balloon systems, certain lesions are inaccessible due to variations in the patient's disease process, degree of narrowing, anatomy and vasculature configuration.

Endovascular procedures are even more challenging when the diseased section occurs at a bifurcation in the vessel. For example, significant sized and important side branches have presented serious difficulties in the angioplasty procedure because closure of a significant sized side branch, which supplies a significant amount of blood to an organ or muscle bed, can occur in 10–20% of cases during angioplasty of the adjacent main branch. This is because a single balloon cannot effectively enter and open these side branches, as well as keep open the main vessel, even when techniques such as the "kissing" balloon, or double wire technique are used. These difficulties occur in any area where acutely angled branching occurs along a bend in an artery. Difficulties are typically encountered, for example, where lesions occur near the origin of the left main coronary artery, the extracranial carotid artery bifurcation, as well as the bifurcation of the abdominal aorta into the right and left iliac arteries, the origin of a brachiocephalic vessel from the transverse aorta, and the origin of the renal arteries from the abdominal aorta.

There are a number of difficulties encountered during angioplasty at a vessel bifurcation. First, when attempting to perform a dilatation in one of the branches of the bifurcated vessel, the inflation of the balloon may cause closure or narrowing of the other adjacent branch. In order to prevent that occurrence, the "kissing balloon" technique has been developed. With this technique, two independent and separate balloon dilatation catheters introduced through the same or different guide catheters are used, side-by-side, one balloon extending into one branch of the bifurcation and the other balloon extending into the other branch of the bifurcation. If the dilatation of the stenosed branch causes the other branch to become constricted, the balloon in that other branch can also be inflated to prevent closure of that other branch. In other variations of the technique, the two balloons may be inflated sequentially or simultaneously so as to keep both branches open. Typically, in such an arrangement, the proximal ends of the balloons are disposed within the common trunk and their proximal ends touch or "kiss". This method and the apparatus used to perform it are described in U.S. Pat. Nos. 4,896,670 and 5,143,093. Variations on this method which employ a single catheter are described in U.S. Pat. Nos. 4,413,989 and 5,413,581. The '989 patent discloses a "Y" shaped balloon transported on the end of a single catheter, and the '581 patent discloses a separate guide wire that can be deployed into one vessel branch so as to protect it or allow subsequent insertion of another balloon catheter while the other vessel branch is dilated using a balloon.

In another treatment method, two guide wires are introduced, again percutaneously through one guide catheter, and in such a way that they separate in front of the ramification. On the one guide wire, a so-called "monorail" catheter is first introduced into one branch of the ramification. The stricture site in this branch is dilated using the balloon of the catheter, and the catheter is thereafter completely withdrawn. On the other guide wire, another balloon dilatation catheter is now introduced into the other branch of the ramification, and the stricture in this other branch is dilated. This technique may be sequential (as previously stated) or both balloons may be inserted to permit simultaneous inflation. Both methods enable dilation of both ramifications, continued access to both ramifications, and use of a small bore guide catheter.

Another challenge presented at a bifurcated vessel is the need for highly accurate placement of an endovascular device. This is particularly important when placing a stent, covered stent, stent graft or other implant at a bifurcation. If the vessel is diseased at the bifurcation, the stent, must be placed in a vessel branch and over the diseased region without intruding into the other vessel branch. Very frequently the disease extends from the trunk into one or both of the vessel branches. As many as three separate stents may be placed at the bifurcation, one in each branch and one in the trunk. The separate insertion and accurate placement of each stent is both time consuming, and in some cases, very difficult to do.

SUMMARY OF THE SUMMARY

The present invention is an endovascular catheter which delivers endovascular devices to bifurcated, dividing, or branching vessels. More particularly, the invention is a catheter which is bifurcated at its distal end such that the catheter may be guided to bifurcated vasculature and each branch of its bifurcated end may then be guided into separate vessel branches. Devices such as balloons, stents, stent grafts, or implants may be carried on the distal ends of the catheter. Separate endovascular devices may be carried on either, or both of the bifurcated catheter ends and placed in the vessel branches. In the alternative, a device may be carried on the catheter for accurate placement in the vessel trunk. The bifurcated catheter ends are guided into each vessel branch until the endovascular devices are in place, or the "crotch" of the catheter makes contact with the junction of the two vessel branches and does not permit the catheter to advance any further into the vessel. Once mounted on each arm of the bifurcated catheter, precise alignment of the endovascular device with respect to the diseased vessel can thus be achieved. The endovascular device(s) may be deployed with assurance that they are accurately placed with respect to the vessel juncture.

An object of the invention is to reduce the difficulty and time required to place devices at bifurcated vessels by deploying them accurately. The catheter need only be inserted and guided to the diseased vessel once during the procedure. When the bifurcation is reached, each catheter branch is separately advanced and guided into each vessel branch over the previously placed guide wire and all the endovascular devices are carried into the proper position for deployment. The endovascular devices may be deployed together or in sequence.

Another object of the invention is to reduce the risk of damage to vessels. The placement of the guide wires into each branching vessel enables the bifurcated catheter to be moved into each vessel, simultaneously, easily and facilely. Thus, the branches may be dilated easier, quicker, with less trauma, and with a substantial reduction in the risk of dissection, especially with the delivery of a stent.

Yet another object of the invention is to enable integral, bifurcated or branched endovascular devices to be deployed. An endovascular device can be shaped and sized to fit the entire bifurcated or branched vasculature, or any portion thereof. The two branches of the endovascular device are carried by the respective bifurcated catheter ends into the respective vessel branches. The body of the device encircles the distal end of the catheter prior to its bifurcation, and the body is positioned in the vessel trunk. An integral balloon, stent or implant may thus be deployed over the entire vessel wall, proximal and distal to its bifurcation.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 1 is a pictorial view of a catheter system which employs the present invention to delivery endovascular devices to bifurcated vasculature;

FIG. 2 is a view in cross section of the distal end of the catheter system of FIG. 1 before deployment in the separate branches of a bifurcated vessel;

FIG. 7 is a pictorial view of the bifurcated catheter of FIG. 5 before deployment of the stents;

FIG. 8 is a pictorial view of the bifurcated catheter of FIG. 5 after one stent is deployed;

FIG. 9 is a view in cross-section of the bifurcated catheter of FIG. 5 after one stent is deployed;

FIG. 12 is a partial view in cross section of the distal end of an alternative embodiment of the catheter system of FIG. 1.

DESCRIPTION OF THE PREFERRED EMBODIMENT

Figure 3:
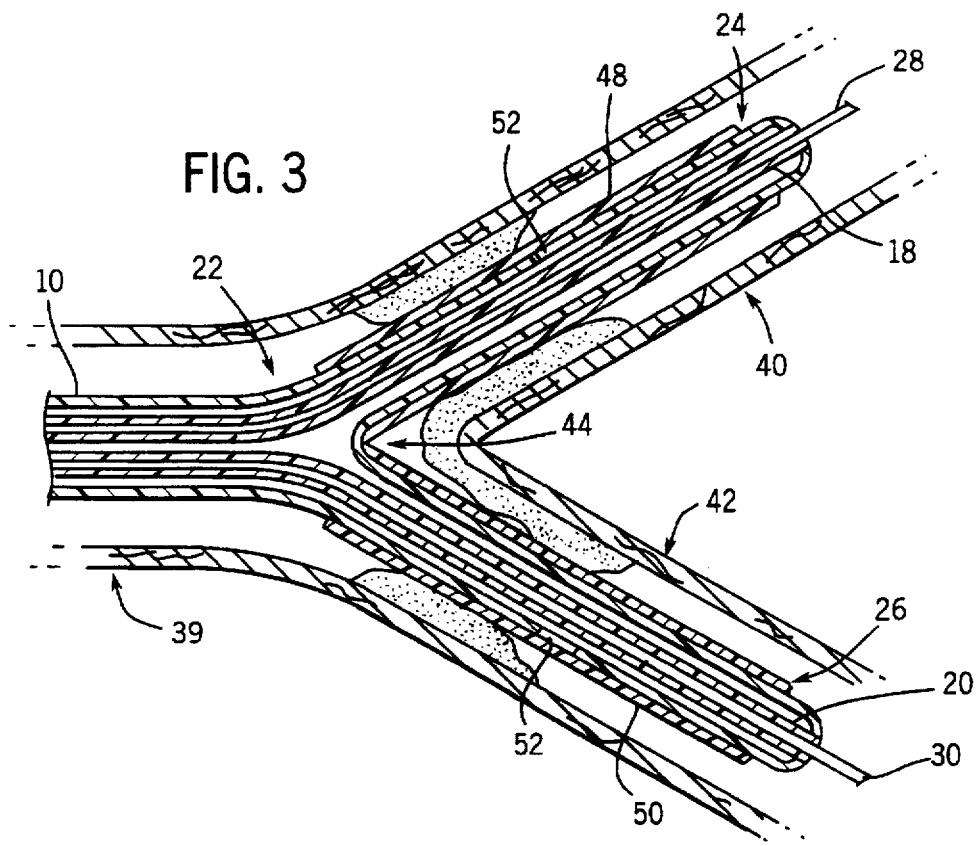
FIG. 3 is a view in cross section of the distal end of the catheter system of FIG. 1 showing the bifurcated catheter deployed in separate vessel branches.

Referring particularly to FIG. 1, a first preferred embodiment of the invention deploys balloons in the branches at a vessel bifurcation. The endovascular catheter system includes a flexible, plastic catheter shaft 10 having a length suitable for reaching the diseased vasculature from the selected percutaneous vessel entry point. At its proximal end the catheter shaft 10 connects to a fixture 12 that defines an inlet to the interior of the catheter shaft 10 and connects that inlet through a tube 14 to a valve 16. The fixture 12 also provides two openings which enable two guidewire shafts 18 and 20 to exit from the proximal end of the catheter shaft 10.

The distal end of the catheter shaft 10 divides to form a bifurcated catheter indicated generally at 22. Two catheter branches 24 and 26 are thus formed at the distal end of the catheter system and the guide wire shafts 18 and 20 extend into the respective catheter branches 24 and 26. Guide wires 28 and 30 extend through lumens formed in the respective guide wire shafts 18 and 20 and terminate at their proximal ends with grips 32 and 34 which enable them to be manipulated. Tapered ends 36 and 38 are attached to the distal ends of the respective guide wires 28 and 30 to enable them to be manipulated and extended through vessels by maneuvering the respective grips 32 and 34 at their proximal ends.

As shown best in FIG. 2, the bifurcated catheter 22 enables one guide wire shaft 18 to be guided through a vessel trunk 39 into one vessel branch 40, and the other guide wire shaft 20 to be separately guided into another vessel branch 42. As shown in FIG. 3, the bifurcated catheter 22 is positioned with the catheter branches 24 and 26 in the respective vessel branches 40 and 42. The crotch 44 of the bifurcated catheter 22 engages the bifurcated vessel wall and serves as a means for precisely aligning the catheter 22 within the vessel.

Figure 4:
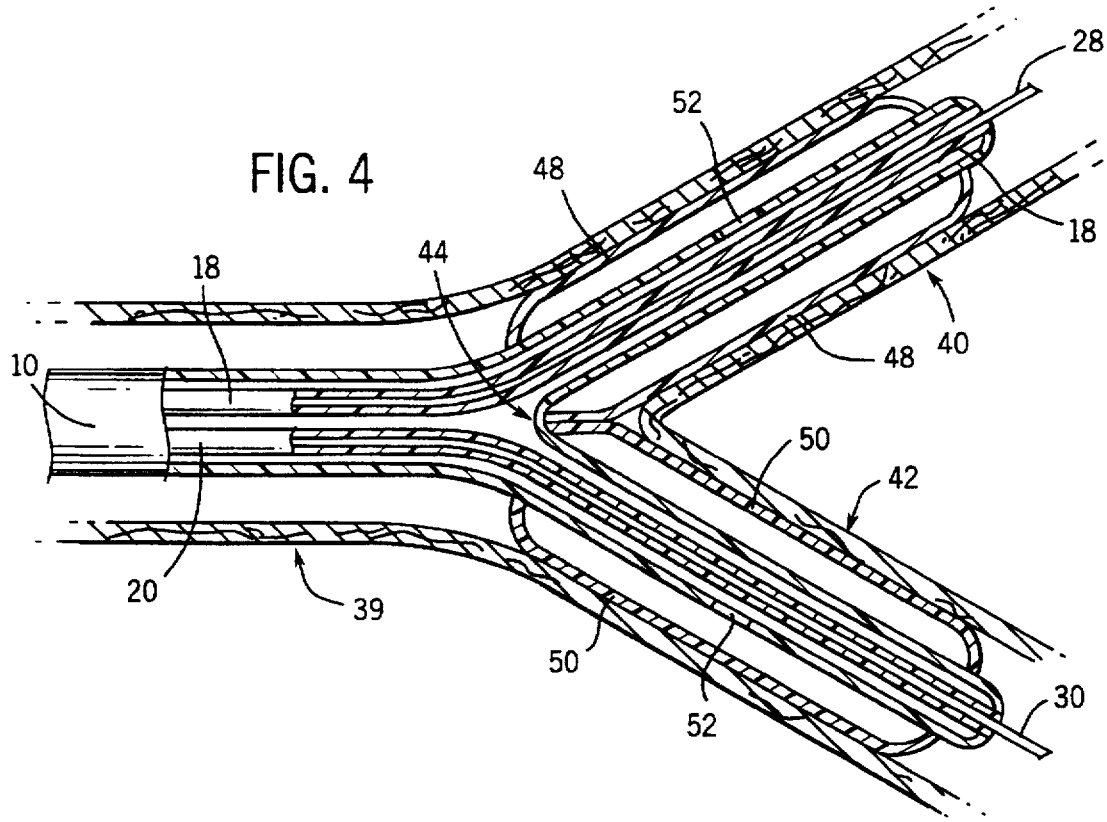
FIG. 4 is a pictorial view of the distal end of the catheter system of FIG. 1 delivering dilation balloons to the bifurcated vessel.

Referring particularly to FIGS. 2–4, dilation balloons 48 and 50 are mounted on the respective catheter branches 24 and 26. The length, diameter and precise location of each balloon 48 and 50 are selected for the particular diseased vessel being treated. In the embodiment shown the stenotic region extends around the juncture of the two vessel branches 40 and 42 and the balloons 48 and 50 are positioned to "kiss" when they are inflated as shown in FIG. 4.

The balloons 48 and 50 are inflated by injecting fluid into them through the valve 16 as shown in FIG. 1. The fluid passes through the interior of the catheter shaft 10 which serves as an inflation lumen and flows into the interior of each catheter branch 24 and 26. Openings 52 are formed in each catheter branch 24 and 26 beneath the balloons 48 and 50, and the fluid passes through these openings 52 to inflate the balloons as depicted in FIG. 4. As is well known in the art, the pressure of the inflation fluid is precisely controlled to expand the vessel lumen in the desired manner.

It should be apparent to those skilled in the art that the bifurcated catheter system enables many different angioplasty procedures to be performed at or near bifurcated vessels. If the stenosis is in one vessel branch, a single balloon may be mounted on the corresponding catheter branch and inflated when the bifurcated catheter 22 is properly positioned. In this case the engagement of the crotch 44 of the catheter serves as a means for precisely aligning the balloon with respect to the vessel bifurcation. Also, if the stenosis extends into the vessel trunk 39, a separate balloon may be mounted to the catheter shaft 10, proximal its bifurcation. And finally, if both vessel branches 40 and 42 and the vessel trunk 39 are diseased, a single Y-shaped balloon (not shown) may be mounted to the bifurcated catheter 22 and inflated to dilate the vessel lumen throughout the vessel bifurcation.

It should be apparent to those skilled in the art that the catheter shaft 10 may contain as many lumens as are necessary to inflate the balloons carried at the distal end of the catheter system. In the preferred embodiment described above a single inflation lumen is provided and the balloons are deployed simultaneously by increasing the fluid pressure in this lumen. If simultaneous inflation is not desired as shown in the embodiment of FIG. 1, separate inflation lumens can be formed in the catheter shaft 10 for each balloon. For example, as shown in FIG. 12, the interior of the catheter shaft 10 may be divided into two separate lumens 94 and 96 by a wall 98 which divides its cylindrical volume into two separate parts. This wall 98 terminates at the crotch 44 of the catheter bifurcation.

Figure 5:
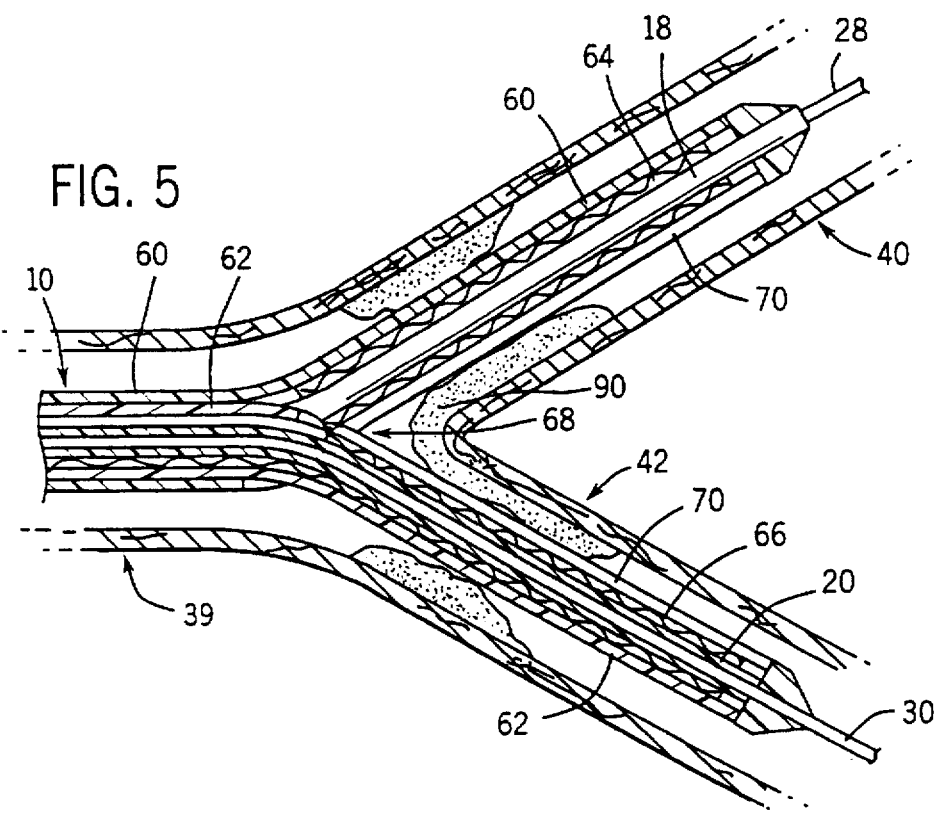
FIG. 5 is a pictorial view of the distal end of a second embodiment of the catheter system of FIG. 1 delivering two stents to the bifurcated vessel.

A second embodiment of the invention for deployment of stents at bifurcated vessels is shown in FIG. 5. In this embodiment the catheter shaft 10 is formed by two coaxial sleeves 60 and 62 which extend from the proximal end of the catheter system to its distal end. The sleeves 60 and 62 bifurcate at the distal end of the catheter, with one sleeve being guided into one vessel branch 40 and the other sleeve 62 being guided into vessel branch 42. Two guide wire shafts 18 and 20 extend through the sleeves 60 and 62, and at the bifurcation, the guide wire shaft 18 extends into the catheter branch formed by sleeve 60 and the guide wire shaft 20 extends into the catheter branch formed by sleeve 62. A self-expanding stent 64 is mounted to the guide wire shaft 18 in one catheter branch and a self-expanding stent 66 is mounted to the guide wire shaft 20 in the other catheter branch. The stents 64 and 66 are designed such that when the surrounding sleeves 60 and 62 are withdrawn, the stents expand radially outward to engage the surrounding vessel wall and dilate the vessel lumen. As is well known in the art, the catheter system is then withdrawn to leave the stents in place where they continue to produce a radially outward force on the vessel to hold the stent in place and keep the vessel lumen open.

As with the first embodiment of the invention, the second embodiment in FIG. 5 is inserted and guided into position using guide wires 28 and 30 in the respective guide wire shafts 18 and 20. After the guide wires 28 and 30 are placed in each vessel branch 40 and 42, the catheter is advanced along them and the sleeves 60 and 62 are guided into the respective vessel branches 40 and 42. The catheter system is properly placed when the crotch 68 of the bifurcated catheter engages the bifurcated vessel wall.

The sleeves 60 and 62 each have a longitudinal cut 70 which extends from their distal ends to the crotch 68. It is these longitudinal cuts 70 which define where the catheter bifurcates, since the inner sleeve 62 exits through the longitudinal cut 70 in the outer sleeve 60 to follow a separate path into the vessel branch 42 as shown in FIG. 7. These same longitudinal cuts 70 enable the sleeves 60 and 62 to be separately withdrawn to deploy the stents 64 and 66 as will now be described.

Referring particularly to FIGS. 8–11, the stents 64 and 66 are deployed in a three step process. As shown in FIGS. 8 and 9, the outer sleeve 60 is first withdrawn as indicated by arrow 84. As the sleeve 60 is withdrawn, the stent 64 expands radially outward against the vessel walls 40. The longitudinal slot 70 in the sleeve 60 enables it to open as it slides over the diverging inner sleeve 62, but it is molded to reclose and assume its circular cylindrical shape after it is withdrawn from the catheter bifurcation.

Figure 10:
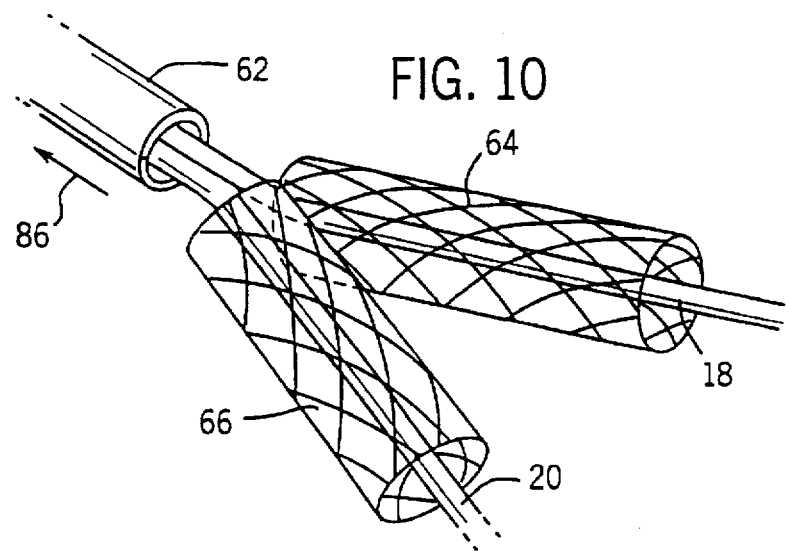
FIG. 10 is a pictorial view of the bifurcated catheter of FIG. 5 after both stents are deployed.
Figure 11:
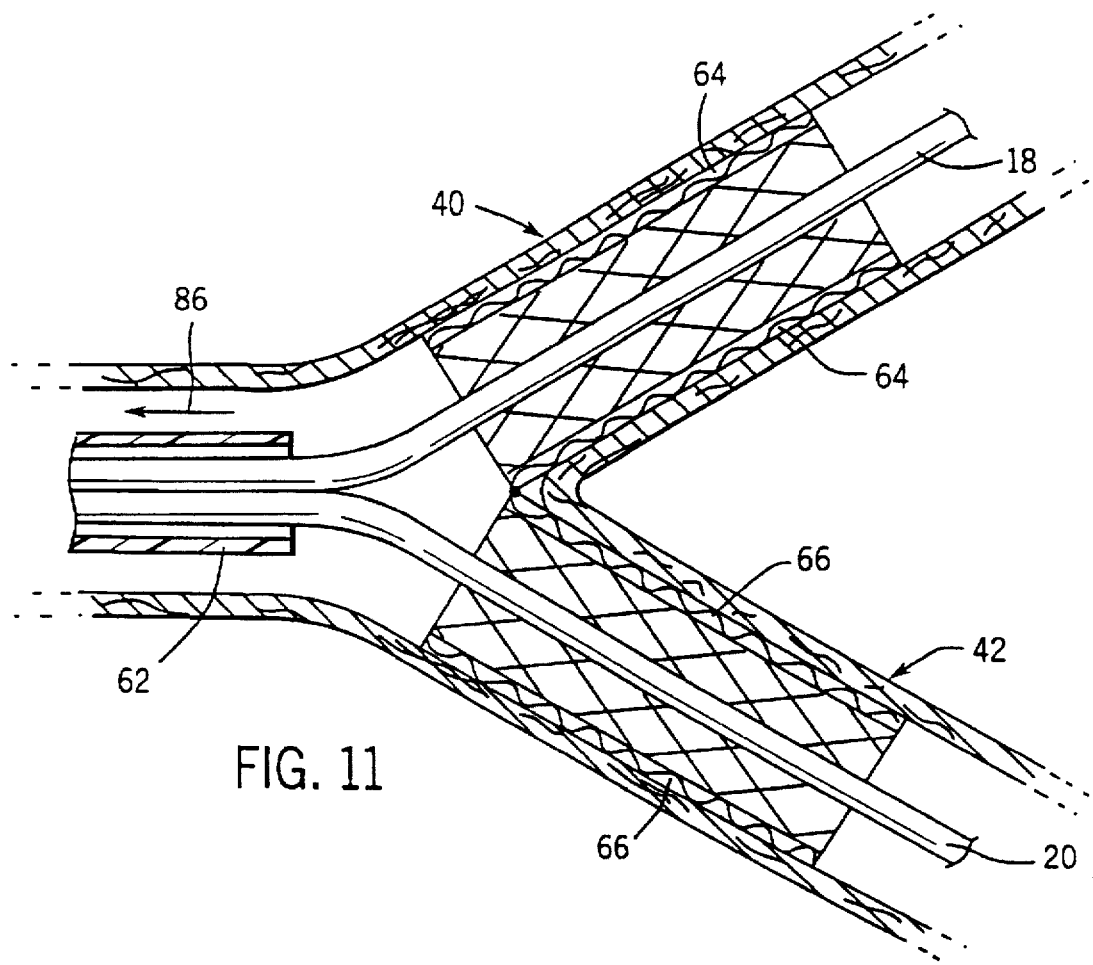
FIG. 11 is a view in cross-section of the bifurcated catheter of FIG. 5 after both stents are deployed.

As shown best in FIGS. 10 and 11, the inner sleeve 62 is then withdrawn as indicated by arrow 86. The stent 66 expands radially outward against the vessel wall 42 as it is released, and it remains in place to provide a supporting infrastructure which keeps the vessel lumen dilated. The final step is to withdraw the guide wire shafts 18 and 20 and the guide wires 28 and 30.

The stents 64 and 66 are substantially separate structures and they may be mounted to the guide wire shafts 18 and 20 such that they are deployed over the diseased section when the catheter crotch 80 engages the vessel bifurcation. In the embodiment shown in FIG. 5, the stents 64 and 66 are fastened together at the crotch 80 to ensure that the stenosis 90 is completely covered at the vessel bifurcation when the stents are deployed as shown in FIG. 11.

Figure 6:
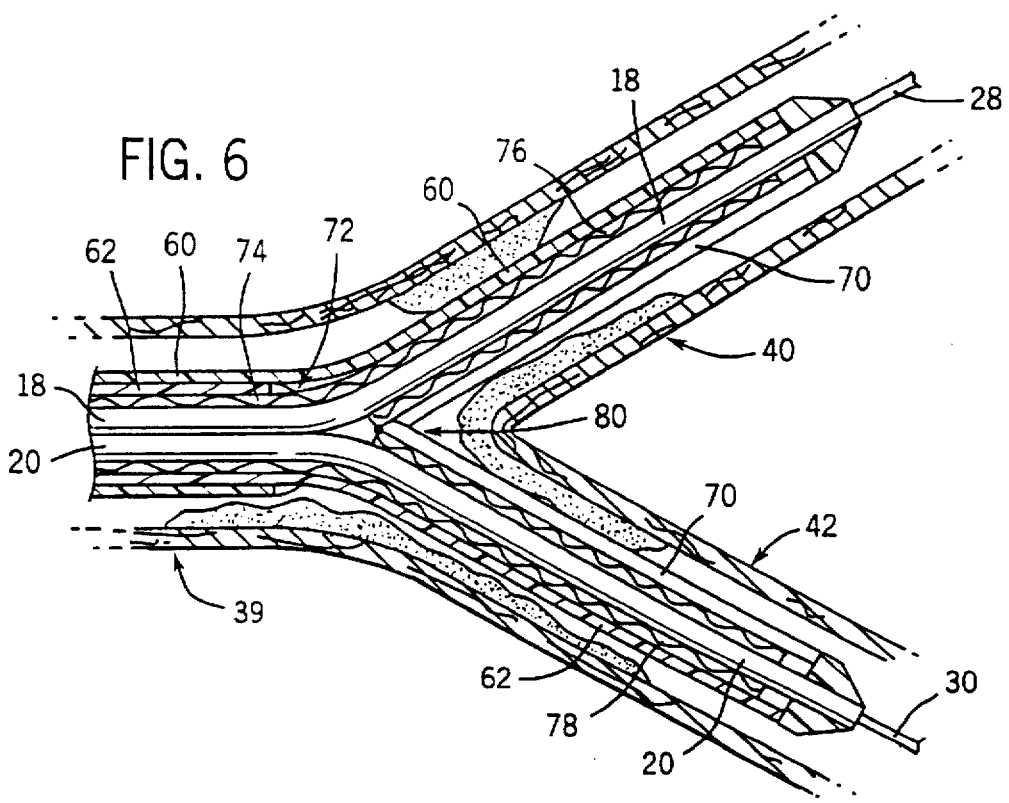
FIG. 6 is a view in cross section of the distal end of another embodiment of the catheter system of FIG. 1 for delivering an integral stent to bifurcated vasculature.

As shown in FIG. 6, the second embodiment of the invention may also be used to deploy an integral, Y-shaped stent 72. This stent 72 has a trunk portion 74 which surrounds both guide wire shafts 18 and 20 and two integrally woven branch portions 76 and 78. The branch portion 76 is supported by the guide wire shaft 18 and follows it into the vessel branch 40, and the branch portion 78 is supported by the guide wire shaft 20 and follows it into the vessel branch 42. The crotch 80 of the integral stent 72 engages the bifurcated vessel wall, and it is deployed by withdrawing the sleeves 60 and 62 as described above. Withdrawal of sleeve 60 deploys the stent branch 76 that expands radially outward to engage the wall of vessel branch 40. Withdrawal of sleeve 62 first deploys the stent branch 78 in the vessel branch 42, and its further withdrawal deploys the stent trunk 74 in the vessel trunk 39.

It should be apparent to those skilled in the art that the bifurcated catheter of the present invention may be used to precisely deploy many types of endovascular devices in vessels. The bifurcated catheter enables devices to be easily deployed in the vessel trunk, in either of its branches, or in any combination thereof. In addition, the crotch of the bifurcated catheter serves as a means to accurately position the endovascular devices with respect to the bifurcation in the vessel.

I claim:

1. An endovascular catheter system which comprises:

a shaft formed from a flexible material suitable for insertion into a blood vessel or othersimiliar conduit;

a bifurcated shaft formed on a distal end of said shaft and having two branches that may be guided into separate vessels;

a first lumen extending through the shaft from a proximal end thereof to its distal end and through one of said bifurcated shaft branches;

a second lumen extending through the shaft from its proximal end to its distal end and through the other one of said bifurcated shaft branches;

a first guide wire inserted through the first lumen for guiding said one of the bifurcated shaft branches into one vessel branch;

a second guide wire inserted through the second lumen for guiding said other one of the bifurcated shaft branches into another vessel branch;

an endovascular device mounted on one of said bifurcated shaft branches; and means for deploying said endovascular device.

2. The endovascular catheter as recited in claim 1 in which the endovascular device is a balloon, and the means for deploying it includes a third lumen which extends through the shaft and into said bifurcated shaft branch to which the balloon is mounted.

3. The endovascular catheter as recited in claim 2 which includes a second balloon mounted to the other of said bifurcated shaft branches and a fourth lumen extends through the shaft and into the other of said bifurcated shaft branches to control the deployment of the second balloon.

4. The endovascular catheter as recited in claim 3 which includes a third balloon mounted to the shaft adjacent the bifurcated shaft branches, and means for deploying the third balloon.

5. The endovascular catheter as recited in claim 1 in which the endovascular device is a self-expanding stent, and the means for deploying it includes a sleeve that surrounds the stent and extends through said shaft to its proximal end.

6. The endovascular catheter as recited in claim 5 which includes a second stent mounted to the other of said bifurcated shaft branches and a second sleeve that surrounds the second stent and extends through the shaft to its proximal end.

7. The endovascular catheter as recited in claim 5 in which the sleeve has a longitudinal cut therein which enables the sleeve to be withdrawn from the bifurcated shaft branch to deploy the stent.

8. The endovascular catheter as recited in claim 5 in which the two sleeves each have a longitudinal cut therein which enables them to be withdrawn from the bifurcated shaft branches to deploy their respective stents.

9. The endovascular catheter as recited in claim 6 in which the two stents are fastened together.

10. The endovascular catheter as recited in claim 6 in which a third stent surrounds the shaft adjacent the two branches and one of said sleeves surrounds the third stent.

11. The endovascular catheter as recited in claim 10 in which the three stents are fastened together to form a single endovascular device.

12. The endovascular catheter as recited in claim 1 in which the endovascular device is a stent with a thermal memory that causes it to deploy by expanding.

\* \* \* \* \*